(12) United States Patent
Hsieh

(10) Patent No.: US 11,158,095 B2
(45) Date of Patent: Oct. 26, 2021

(54) SYSTEM AND METHOD FOR REDUCING ARTIFACT BLOOM IN A RECONSTRUCTED OBJECT

(71) Applicant: GENERAL ELECTRIC COMPANY, Schenectady, NY (US)

(72) Inventor: Jiang Hsieh, Brookfield, WI (US)

(73) Assignee: General Electric Company, Schenectady, NY (US)

( * ) Notice: Subject to any disclaimer, the term of this patent is extended or adjusted under 35 U.S.C. 154(b) by 267 days.

(21) Appl. No.: 16/112,091

(22) Filed: Aug. 24, 2018

(65) Prior Publication Data
US 2020/0066010 A1 Feb. 27, 2020

(51) Int. Cl.
G06T 5/00 (2006.01)
G06T 11/00 (2006.01)
A61B 6/02 (2006.01)

(52) U.S. Cl.
CPC ............ G06T 11/008 (2013.01); A61B 6/027 (2013.01); G06T 5/002 (2013.01)

(58) Field of Classification Search
CPC . G06T 11/008; G06T 5/002; G06T 2211/404; A61B 6/027; A61B 6/032
See application file for complete search history.

(56) References Cited

U.S. PATENT DOCUMENTS

| | | | |
|---|---|---|---|
| 7,515,678 B2 | 4/2009 | Hsieh et al. | |
| 8,699,812 B2 | 4/2014 | Hsieh et al. | |
| 2003/0147497 A1* | 8/2003 | Avinash | G06T 5/007 378/98.9 |
| 2007/0092056 A1* | 4/2007 | Flohr | A61B 6/482 378/4 |
| 2012/0076377 A1* | 3/2012 | Dutta | A61B 6/032 382/131 |
| 2012/0207270 A1* | 8/2012 | Flohr | G06T 5/50 378/5 |
| 2012/0314922 A1* | 12/2012 | Hsieh | G06T 11/008 382/131 |
| 2016/0307340 A1* | 10/2016 | Allmendinger | G06T 11/008 |
| 2019/0213715 A1* | 7/2019 | Li | A61B 6/482 |

OTHER PUBLICATIONS

Scientific Reports: Blooming Artifact Reduction in Coronary Artery Calcification by a New De-blooming Algorithm: Initial Study published on May 2, 2018 by Ping Li, et al.
Proceedings of Spie: Removing Blooming Artifacts With Binarized Deconvolution in Cardiac CT, 2014, by Christian Hofmann, et al.

* cited by examiner

Primary Examiner — Marcus Hammonds

(57) ABSTRACT

A system for reducing artifact bloom in a reconstructed image of an object is provided. The system includes an imaging device, and a controller. The imaging device is operative to obtain one or more slices of the object. The controller is in electronic communication with the imaging device and operative to: generate the reconstructed image based at least in part on the one or more slices; and de-bloom one or more regions within the reconstructed image based at least in part on a contrast medium enhancement across at least part of a volume of the object.

15 Claims, 6 Drawing Sheets

SYSTEM AND METHOD FOR REDUCING ARTIFACT BLOOM IN A RECONSTRUCTED OBJECT

BACKGROUND

Technical Field

Embodiments of the invention relate generally to medical imaging systems, and more specifically, to a system and method for reducing artifact bloom in a reconstructed object.

Discussion of Art

In many computer tomography ("CT") imaging systems, an x-ray source/tube emits a fan-shaped beam toward an object/subject, e.g., a patient or piece of luggage. The beam, after being attenuated by the object, impinges upon a radiation detector. The intensity of the attenuated beam radiation received at the detector is typically dependent upon the attenuation of the x-ray beam by the object. Many radiation detectors in CT systems often include an array of individual detector elements/cells which produce separate electrical signals indicative of the attenuated beam received by each detector element. The electrical signals are transmitted to a data processing system for analysis to ultimately produce an image/projection. Generally, the x-ray source and the detector are rotated about the object within an imaging plane via a gantry, with the imaging system obtaining a plurality of two-dimensional ("2D") projections of the object over a three-hundred-and-sixty-five degree (365°) range. After receiving the projections, the data processing system generates a three-dimensional ("3D") image/model of the object via tomographic reconstruction.

Coronary CT angiography ("CCTA") is a form of CT which concerns the imaging of blood vessels, also referred to herein simply as "vessels". Typically, CCTA is used to assess the integrity of a deployed stent and/or the degree of stenosis/plaque of a blood vessel. Both stents and stenosis result in high intensity Hounsfield ("HU") values in x-ray images, which in turn, often causes blooming in the 2D projections and/or reconstructed 3D image. As used herein, the terms "blooming", "blooming effect", "artifact bloom" and "artifact blooming" refer to a type of imaging artifact which causes objects to appear brighter and/or larger than reality. As will be understood, blooming often negatively impacts the assessment of the degree of stenosis within the blood vessel, and/or the integrity of a stent, to include stenosis and restenosis inside of the stent.

Several methods have been developed to mitigate blooming in CT, such as dynamic x-ray focal spot deflection (also known as "focal spot wobble"), by modifying the sampling/projection frequency and/or spatial resolution of the projections and/or 3D image. While such methods, when combined with a high-resolution reconstruction kernel, have proven effective at reducing blooming effects due to calcium and/or stents, such technologies, however, often produce increased noise in the projections and/or 3D image, which in turn, usually results in the object receiving a higher radiation dose when certain noise level need to be maintained.

Many tomographic reconstruction processes dictate that the rate of noise increase is much higher than the increase in the spatial resolution. Accordingly, the system resolution is often artificially lowered to ensure the object is not masked by the presence of noise. To overcome such difficulty, iterative calcium de-blooming methods have been proposed which are based on the assumption that each calcification consists of a compact region having constant density and attenuation. Such an assumption, however, is often violated in clinical conditions, and even less valid in the case of a stent.

Other proposed methods for addressing the aforementioned noise/spatial resolution issue check for the presence and consistency of edges within a projection, and/or 3D image, over a wide range prior to any edge-enhancement operations. Although such methods are effective in reducing the appearance of blooming effects, the effectiveness of such methods may be compromised when the intensity of an iodine-enhanced region overlaps the intensities of a region of interest ("ROI"). Consequently, when a de-blooming method is applied, the edge-enhancement operations are often applied to both calcified plaque and/or stents within a vessel, as well as iodine contrast enhanced vessels/chambers, which usually reduces the depicted width of the vessel such that vessel looks narrower than reality. As will be appreciated, such narrowing of a vessel is usually undesirable as the evaluation of stenosis is often based on the percentage narrowing of the vessel, as opposed to the absolute size of the calcium deposit.

What is needed, therefore, is an improved system and method for reducing artifact bloom in a reconstructed image of an object.

BRIEF DESCRIPTION

In an embodiment, a system for reducing artifact bloom in a reconstructed image of an object is provided. The system includes an imaging device, and a controller. The imaging device is operative to obtain one or more slices of the object. The controller is in electronic communication with the imaging device and operative to: generate the reconstructed image based at least in part on the one or more slices; and de-bloom one or more regions within the reconstructed image based at least in part on a contrast medium enhancement across at least part of a volume of the object.

In another embodiment, a method for reducing artifact bloom in a reconstructed image of an object is provided. The method includes determining an intensity threshold based at least in part on a contrast medium enhancement across at least part of a volume of the object. The method further includes identifying one or more regions within the reconstructed image via the intensity threshold. The method further includes de-blooming the one or more regions.

In yet another embodiment, a non-transitory computer readable medium storing instructions is provided. The stored instructions adapt a controller to: determine an intensity threshold based at least in part on a contrast medium enhancement across at least part of a volume of an object in a reconstructed image; identify one or more regions within the reconstructed image via the intensity threshold; and de-bloom the one or more regions.

In still yet another embodiment, a controller is provided. The controller is operative to: generate a reconstructed image based at least in part on one or more slices of a patient obtained by an imaging device; and locally de-bloom one or more calcified plaque regions within the reconstructed image.

DRAWINGS

The present invention will be better understood from reading the following description of non-limiting embodiments, with reference to the attached drawings, wherein below:

DETAILED DESCRIPTION

Figure 1:
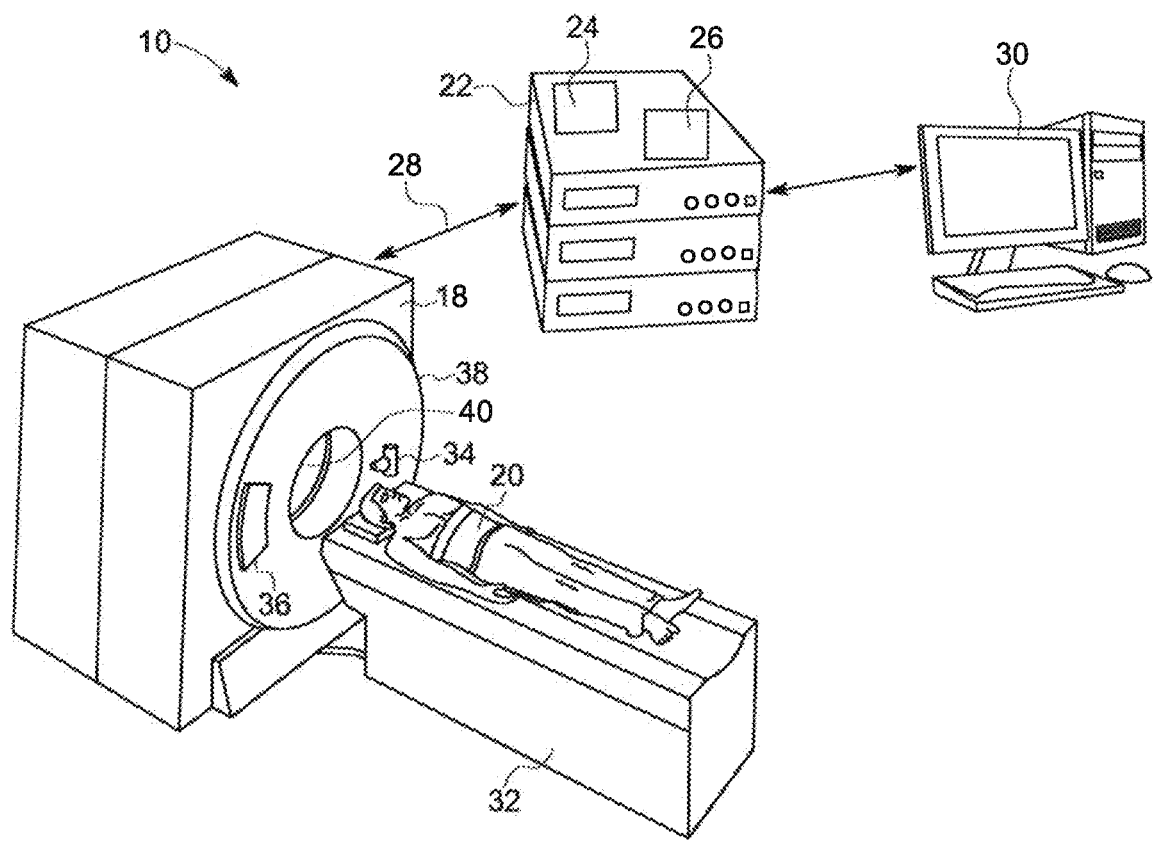
FIG. 1 is a schematic diagram of a system for reducing artifact bloom in a reconstructed object, in accordance with an embodiment of the present invention.

Reference will be made below in detail to exemplary embodiments of the invention, examples of which are illustrated in the accompanying drawings. Wherever possible, the same reference characters used throughout the drawings refer to the same or like parts, without duplicative description.

As used herein, the terms "substantially," "generally," and "about" indicate conditions within reasonably achievable manufacturing and assembly tolerances, relative to ideal desired conditions suitable for achieving the functional purpose of a component or assembly. As used herein, "electrically coupled," "electrically connected," and "electrical communication" mean that the referenced elements are directly or indirectly connected such that an electrical current may flow from one to the other. The connection may include a direct conductive connection, i.e., without an intervening capacitive, inductive or active element, an inductive connection, a capacitive connection, and/or any other suitable electrical connection. Intervening components may be present. The term "real-time," as used herein, means a level of processing responsiveness that a user senses as sufficiently immediate or that enables the processor to keep up with an external process. As further used herein, the terms "imaging procedure" and/or "medical imaging procedure" refer to a medical procedure that involves an imaging system to assist in accomplishing one or more tasks such as, by way of non-limiting examples, deploying/installing a stent into a blood vessel, locating an ulcer, imaging a clogged artery, suturing a patient, and/or other medical processes. As used herein with respect to de-blooming, the term "undershooting" refers to the under-correction of blooming effects, e.g., the brightness is not reduced enough to accurately reflect the true shape of the object/material generating the blooming effect. Similarly, the term "overshooting", as used herein with respect to de-blooming, refers to the over-correction of blooming effects, e.g., the brightness is reduced too much to accurately reflect the true shape of the object/material generating the blooming effect.

Additionally, while the embodiments disclosed herein are described with respect to an X-ray based imaging system, e.g., CT imaging system, it is to be understood that embodiments of the present invention are equally applicable to other devices and/or imaging systems which utilize a contrast agent to enhance image quality. Further, embodiments of the present invention related imaging systems may be used to analyze objects within any material which can be internally imaged, generally. As such, embodiments of the present invention are not limited to analyzing objects within human tissue.

As will be explained in greater detail below, embodiments of the present invention provide for systems and methods of reducing artifact bloom by dynamically determining an appropriate threshold to separate iodine enhancement and calcified plaque. The threshold may be determined globally, i.e., based on an entire volume, as opposed to traditional approaches which generally employ a slice-by-slice approach. Thus, some embodiments of the present invention provide for the isolation of iodine enhancement in a cardiac chamber and/or major blood vessel, as well as reduce the impact of bony structures in a reconstructed image.

Figure 5:
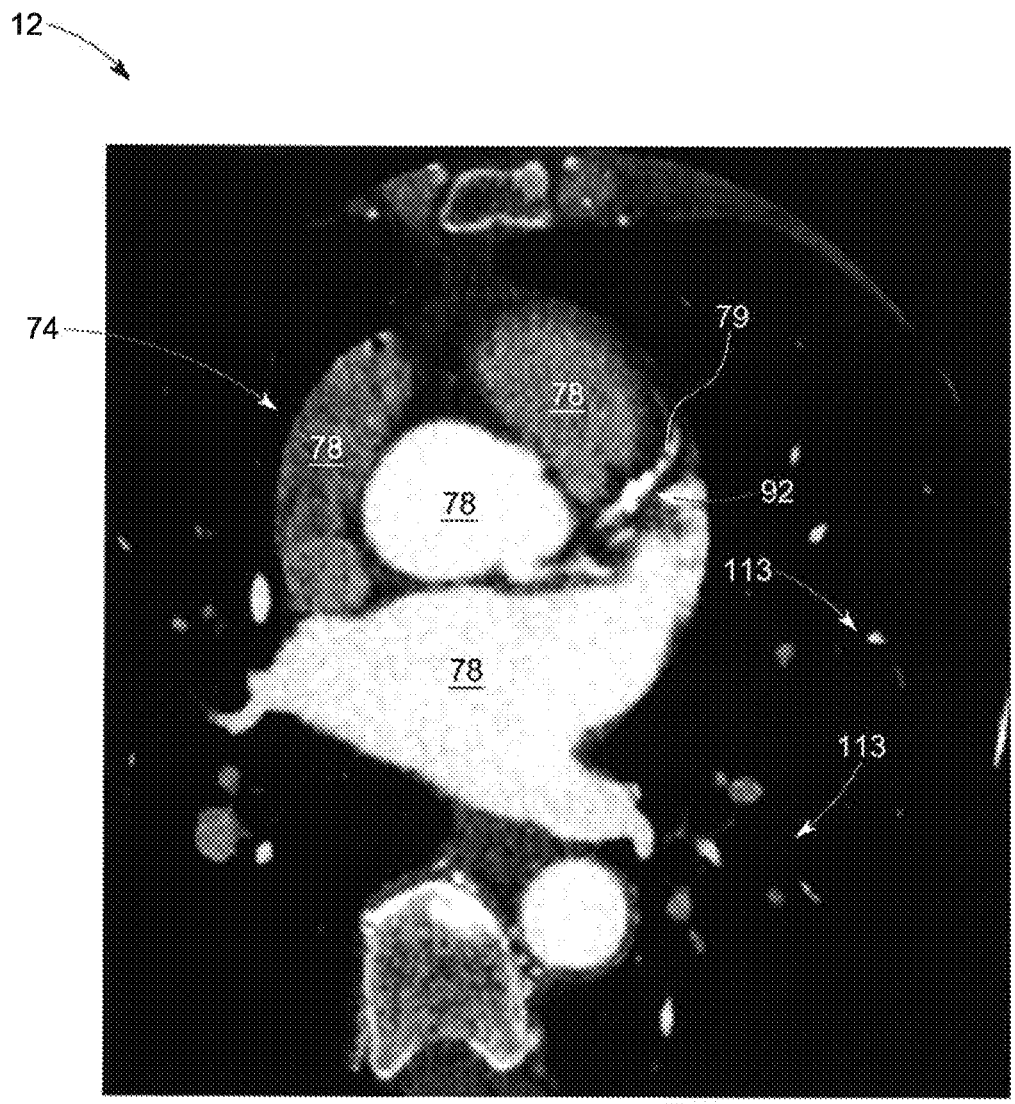
FIG. 5 is a depiction of an original reconstructed image generated by the system of FIG. 1, in accordance with an embodiment of the present invention.
Figure 6:
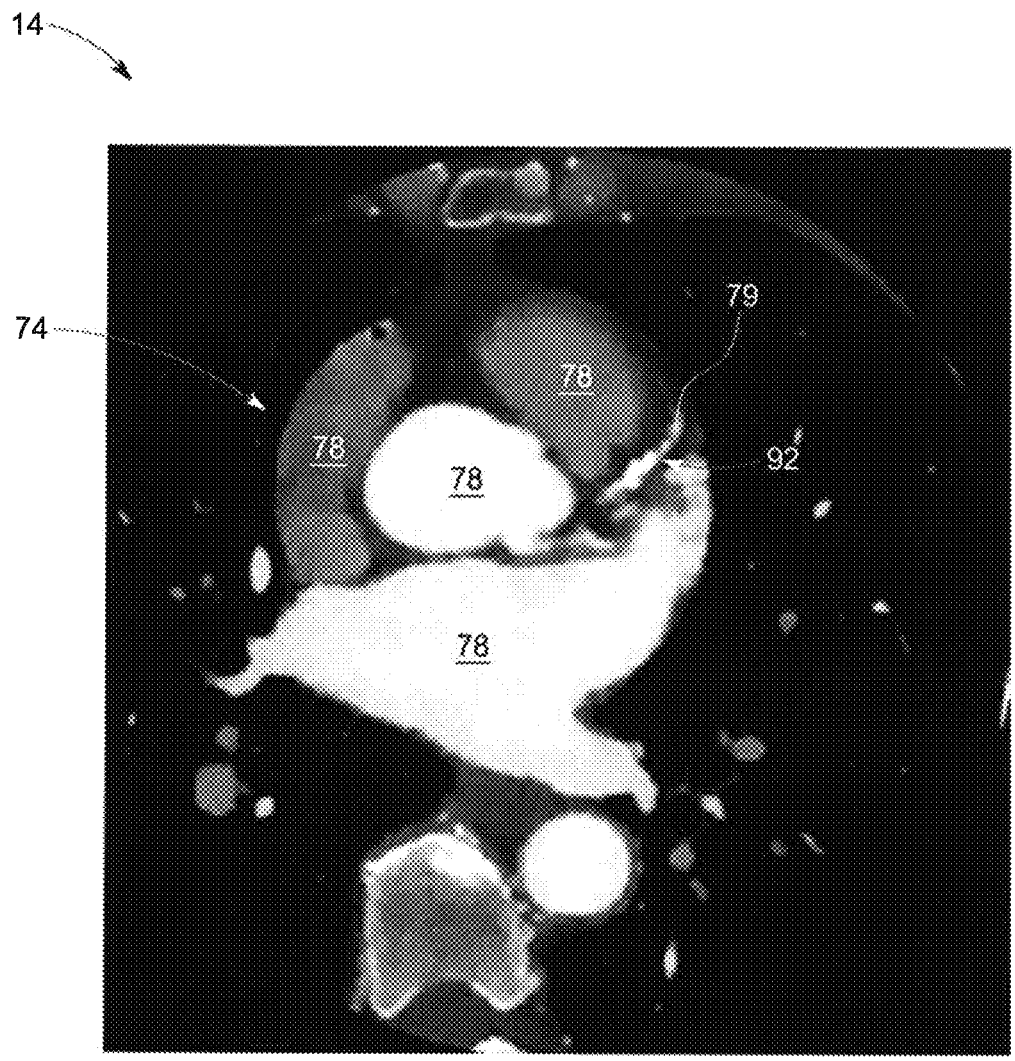
FIG. 6 is a depiction of a noiseless reconstructed image generated by the system of FIG. 1, in accordance with an embodiment of the present invention.
Figure 7:
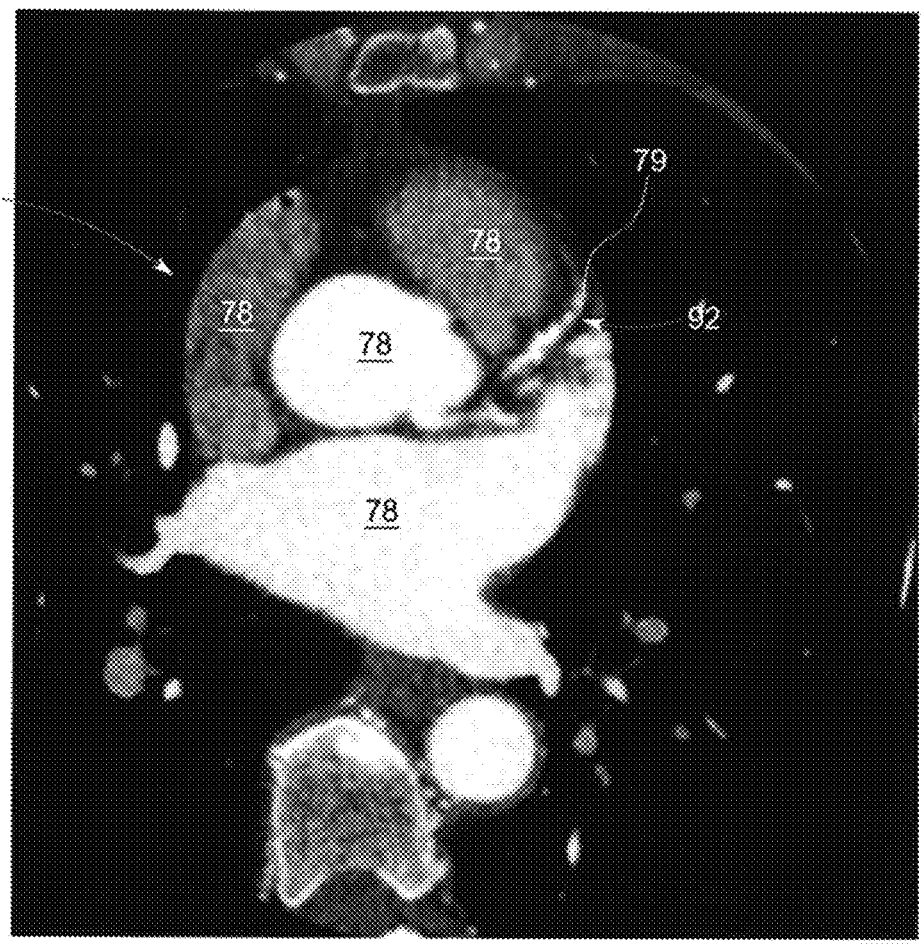
FIG. 7 is a depiction of a de-bloomed reconstructed image generated by the system of FIG. 1, in accordance with an embodiment of the present invention.

Accordingly, referring now to FIG. 1, the major components of a system/imaging system 10 for reducing artifact bloom in a reconstructed image 12, 14, 16 (FIGS. 5-7), in accordance with an embodiment of the present invention, are shown. As shown in FIG. 1, the system 10 includes a detector assembly 18 that is utilized to scan an object/subject/patient 20, and a controller 22, which includes at least one processor 24 and a memory device 26. The controller 22 may electronically communicate with the detector assembly 18 via one or more communication links 28 over which data generated by the detector assembly 18 may be passed to the controller 22. As will be appreciated, in embodiments, the imaging system 10 may further include a human-machine interface ("HMI") 30, i.e., a work station, that provides for a user/technologist/physician to interact with the imaging system 10. The imaging system 10 may further include a table 32 for supporting the object 20 during scanning for a medical imaging procedure.

Figure 2:
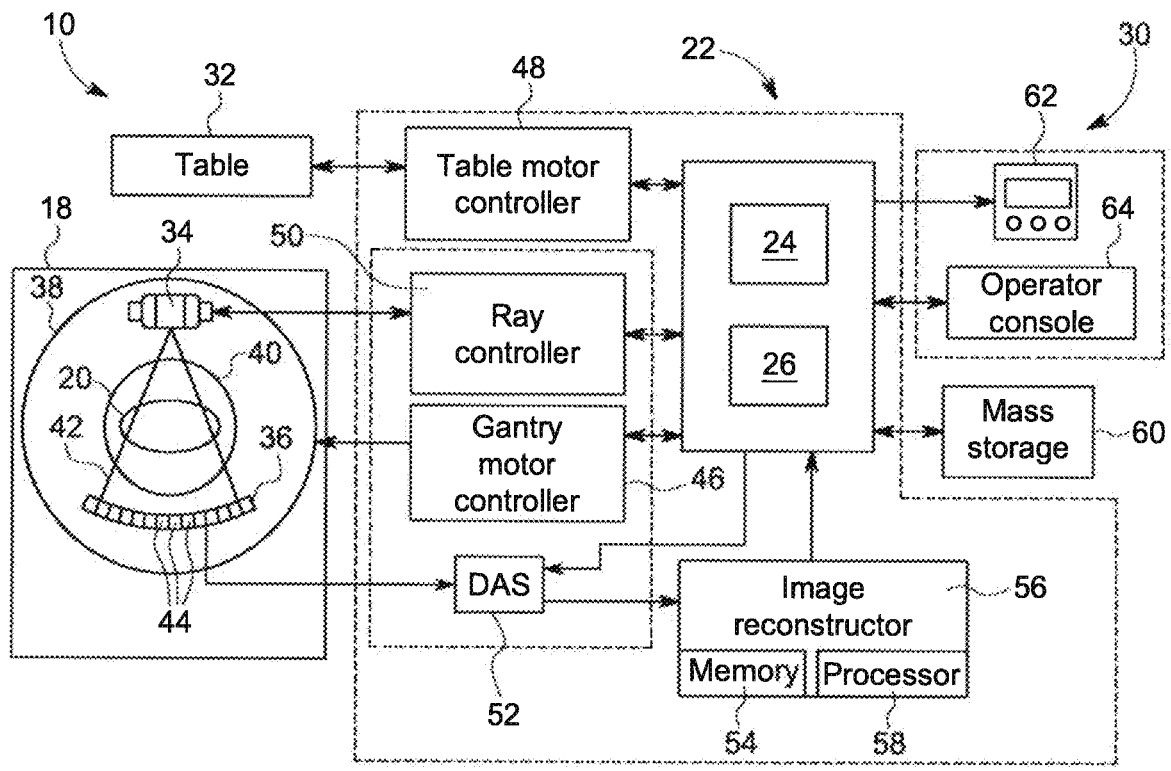
FIG. 2 is a block diagram of the system of FIG. 1, in accordance with an embodiment of the present invention.

As illustrated in FIG. 2, the detector assembly 18 may include an electromagnetic ray generating device/ray generator 34 and a radiation detector 36, which collectively form an imaging device, disposed within a rotating gantry 38 opposite one another. As will be understood, the object 20 is positioned within a bore 40 of the gantry 38, and X-rays 42 generated/projected by the electromagnetic ray generator 34 are received by the radiation detector 36 after having passed through the object 20 while the gantry 38 rotates about the object 20. The radiation detector 36 may include an array of detector elements 44, each of which produces an electric signal representative of an impinging X-ray 42 beam. While the rays 42 generated by the electromagnetic ray generator 34 are disclosed herein as being X-rays, it will be understood that, in embodiments, the rays 42 may be other types of electromagnetic rays/waves, e.g., gamma rays, infrared waves, radio waves, etc.

The controller 22 may include a gantry motor controller 46, a table motor controller 48, a ray controller 50, and a data acquisition system ("DAS") 52. The table motor controller 48 governs actuation of a motor that moves the table 32 in relation to the detector assembly 18, the gantry motor controller 46 controls the rotational direction and/or speed of the gantry 38, the ray controller 50 provides power and timing signals to the ray generator 34, and the DAS 52 samples analog projection data from the detector elements 44 and converts the analog data to digital projection data for subsequent processing. For example, in embodiments, the digital projection data may be loaded from the DAS 52 into a memory 54 device of an image reconstructor 56 where it is used by a processor 58 to reconstruct one or more images via a reconstruction algorithm. The one or more images may then be sent to the HMI 30 and/or a mass storage device 60, e.g., a large computerized data storage apparatus such as a network attached storage ("NAS") device.

The HMI 30 includes a monitor 62 for displaying the reconstructed images, and a console 64, e.g., buttons, dials, a touch screen, a keyboard, and/or a mouse, for receiving command/scanning parameters from an operator of the system 10.

Figure 3:
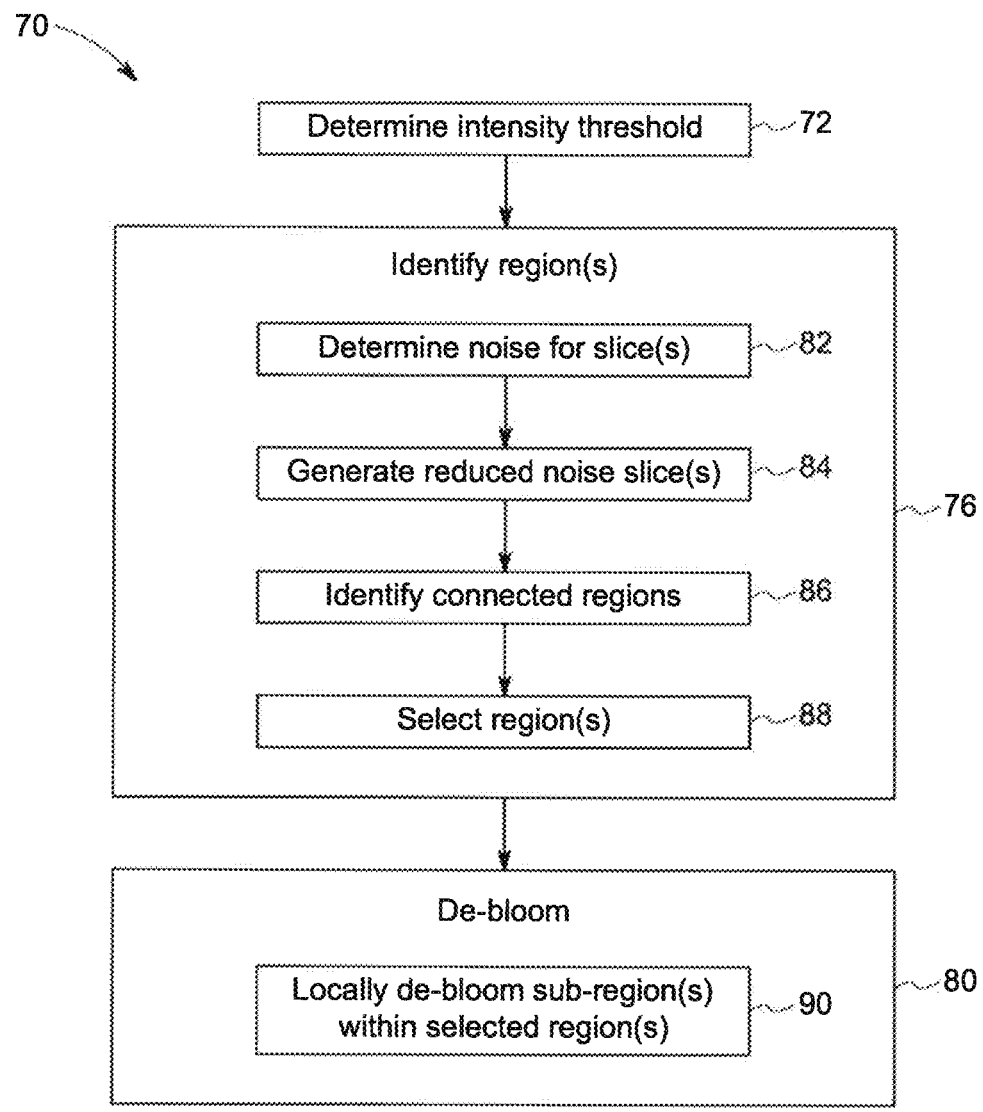
FIG. 3 is a flow chart depicting a method for reducing artifact bloom in a reconstructed object utilizing the system of FIG. 1, in accordance with an embodiment of the present invention.

Turning now to FIG. 3, a method 70 for reducing artifact bloom in a reconstructed image 12, 14, 16 of an object 20 utilizing the system 10, in accordance with an embodiment of the present invention, is shown. The method 70 includes determining 72 an intensity threshold T, e.g., a HU threshold, based at least in part on a contrast medium enhancement across at least part of a volume 74 (FIGS. 5-7) of the object 20; identifying 76 one or more regions 78, 79 within the reconstructed image 12, 14, 16 via the intensity threshold T; and de-blooming 80 the one or more regions 78, 79. In embodiments, identifying 76 the one or more regions 78, 79 may include determining 82 a noise value for one or more slices of the reconstructed image 12, 14, 16. A reduced noise slice may then be generated 84 for each of the one or more slices based at least in part on the noise value of that slice, so that one or more connected regions 78, 79 within each of the reduced noise slices can be identified 86. As used herein, the term "connected region" refers to a grouping of pixels in an image that form an identifiable contiguous region having an area, approximate circumference, and/or approximate radius/diameter that exceeds a pre-defined threshold. One or more of the connected regions, e.g., region 79, having peak intensities that exceed the intensity threshold T may then be selected 88 as the identified one or more regions. As further shown in FIG. 3, in embodiments, de-blooming 80 the one or more regions 79 may include locally de-blooming 90 one or more sub-regions 92 (FIGS. 5-7) of the one or more regions 79, each of the sub-regions 92 having peak intensities that exceed the intensity threshold T.

Figure 4:
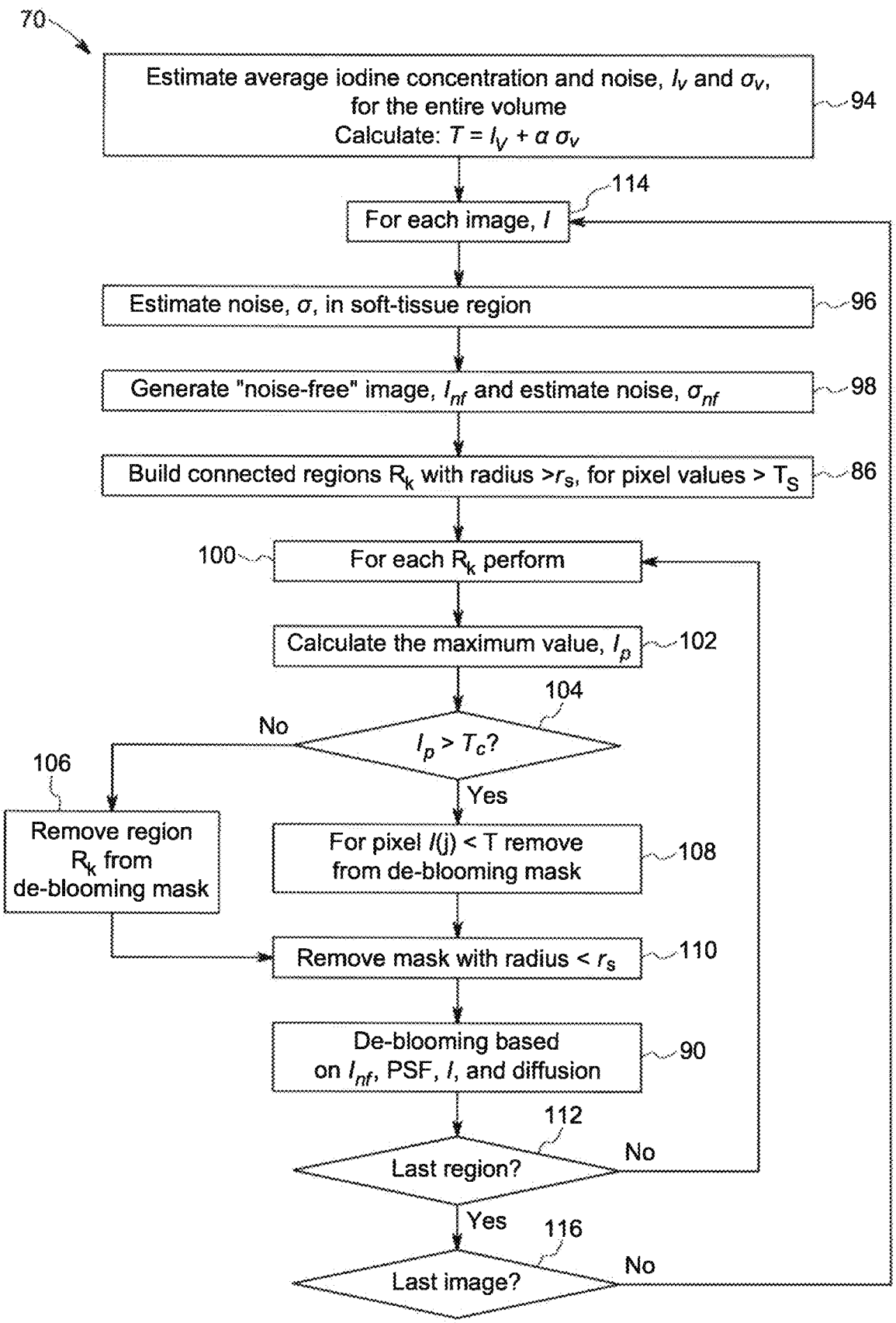
FIG. 4 is another flow chart of the method of FIG. 3, in accordance with an embodiment of the present invention.

Illustrated in FIG. 4 is a more detailed depiction of the method 70, in accordance with an embodiment of the present invention. As stated above, one shortcoming of traditional approaches for de-blooming reconstructed images is their sole reliance of a fixed CT number/HU intensity to guide enhancement operations. For example, during CCTA data acquisitions, it is often difficult to control the iodine enhancement level in cardiac chambers and vessels due to variations in: patient heart output, contrast injection protocols, and/or time delay in data acquisition due to gating. Accordingly, as shown in FIG. 4, the method 70 may include estimating 94 the average iodine enhancement for each scan in order to optimize the intensity threshold T. To accomplish this, a preliminary threshold may be set to identify regions 78, 79 where iodine enhancement takes place. In order to avoid impact of noise on the identification of regions 78, 79, all pixels with CT number values that fall within $u_{low}$, and $u_{high}$ may be marked. Noise estimation may then be performed for the identified region $R_k$ by calculating the standard deviation. Based on the noise estimation 96, the original image 12 may be filtered to produce/generate 98 a noiseless image 14. In embodiments, filtering may be accomplished via an anisotropic diffusion filter and/or other noise reduction operations. As will be understood, by denoting the original image as P(x,y), an iterative anisotropic filter can be described by the following equation:

$$\frac{\partial P(x, y, t)}{\partial t} = div[d(\|\nabla P\|) \cdot \nabla P]$$

where $$d(\xi) = e^{-\frac{\xi^2}{2\eta^2}}$$

is a diffusing function. The parameter η is based on the noise level in the image and the strength of noise reduction, ω. Since the filter is an iterative process, ω is typically a vector. Further, when a multi-resolution approach is used in noise reduction, multiple parameter vectors, $\omega_1, \omega_2, \ldots, \omega_n$, may be used for different resolution settings. As will be understood, the goal of the anisotropic diffusion filtering is to produce the noiseless image 14 to guide the estimation 94 of iodine enhancement. In embodiments, the noise reduction strength may be set much higher than a typical operation where the output is expected to be viewed by a clinician. As will be appreciated, FIGS. 5 and 6 respectively show an unfiltered reconstructed image 12 P(x,y) and a corresponding noiseless image 14 Q(x,y) generated by applying the aforementioned iterative anisotropic filter to the unfiltered reconstructed image 12.

As will be understood, all pixels that satisfy $Q(x,y) > u_{high}$ may be used to calculate contrast enhancement, $I_v$. Notably, bony regions within the image may be inadvertently classified as part of the contrast enhancement region due to their overlapping CT numbers. Accordingly, to reduce the impact of bony regions, embodiments of the present invention may group enhanced pixels into multiple connected regions. Thus, in such embodiments, only regions whose area is larger than a predefined threshold will be included in the contrast calculation. In embodiments, the calculation may be carried out for an entire volume, e.g., cardiac volume, as opposed to a single slice. In embodiments, the calculation may be carried out for at least part of a volume, e.g., two or more slices. The average noise $\sigma_v$ for the enhanced regions in the noiseless image(s) 14 may be calculated in a similar fashion. Thus, the enhancement threshold T can be written as:

$$T = I_v + \alpha \cdot \sigma_v$$

where α is a parameter indicating how many standard deviations away the threshold is set from the mean iodine contrast enhancement value. In order to avoid any impact of residual noise on the operation, the threshold T may be set to be a certain number of standard deviations away from the mean in order to avoid any impact of residual noise on the operation.

Once the enhancement threshold T is established, each of the previously generated connected regions in Q(x,y) may be reexamined, e.g., blocks 100, 102, 104, 108, 106, 110 and 112. In embodiments, erosion and/or dilation operators are applied to each connected region to remove isolated spots 113 (FIG. 5) due to noise and/or other factors. For the remaining regions, the maximum intensity value $I_p$ is calculated 102 for each connected region. If $I_p > I_T$, where $I_T$ is a pre-defined parameter, the region is deemed free of calcium and no further processing need be performed/applied. For connected regions where the maximum intensity is higher than $I_T$, all pixels having intensities higher than T are identified, with some embodiments applying an additional erosion and/or dilation operation to eliminate, and/or reduce, isolated spots.

In embodiments, an initial blooming estimation may be performed by convolving the noiseless image 14 with a point-spread-function ("PSF") of the image generation process. In embodiments, the PSF may be derived from the reconstruction of a thin high-density wire having a diameter significantly smaller than the spatial resolution of the imaging system 10. Embodiments of the present invention may use other methods/forms of PSF. As will be appreciated, the blooming may be estimated initially by the following equation:

$$B(x,y)=Q(x,y)\otimes PSF-\beta\cdot Q(x,y)$$

where an intermediate de-blooming image C(x,y) may be generated by the following equation:

$$C(x,y)=P(x,y)-\varepsilon\cdot B(x,y)$$

To avoid any overshoot and/or undershoot issues, typically related to the deconvolution approach, parameters β and ε in the above equations may be selected such that a slight under-correction of the blooming effect is performed. Some embodiments may further reduce the blooming effect via an anti-diffusion filter. As will be understood, the anti-diffusion filter may be an iterative process similar to the one described above for the anisotropic diffusion filter where a "consistency" condition may be first established for each voxel location. In embodiments, the consistency condition ensures that the intensity gradient is similar for a small number of neighboring voxels along an orientation. For a 2D image, the voxels may be oriented along the x- and y-axis, to include the diagonal directions of the same plane. As will be appreciated, the same concept may be extended into 3D.

Once the consistency condition is determined, the following iterative operation may be performed to arrive at a diffused image C(x,y):

$$\frac{\partial C(x, y, t)}{\partial t} = -div[d(\|\nabla C\|)\cdot \nabla C]$$

where $$d(\xi) = e^{-\frac{\xi^2}{2(M\sigma)^2}}.$$

Thus, the final image, E(x,y) may be produced via blending the original image 12 with the diffused image as follows:

$$E(x,y)=(1-\gamma)\cdot P(x,y)+\gamma\cdot C(x,y)$$

As will be understood, the flowchart depicting method 70 in FIG. 4 shows the aforementioned processes as boxes without expressly showing the iterative nature of such processes for the purpose of clarity, and additionally shows the operations on an image-to-image basis, e.g., the loop formed by boxes 114 and 116. Further, the operations/methods disclosed herein may be carried out in 2D, e.g., sagittal or coronal directions, and 3D, e.g., cardiac volumes.

Finally, it is also to be understood that the imaging systems 10 may include the necessary electronics, software, memory, storage, databases, firmware, logic/state machines, microprocessors, communication links, displays or other visual or audio user interfaces, printing devices, and any other input/output interfaces to perform the functions described herein and/or to achieve the results described herein, which may be accomplished in real-time. For example, as previously mentioned, the systems may include at least one processor and system memory/data storage structures, which may include random access memory (RAM) and read-only memory (ROM). The at least one processor of the system may include one or more conventional microprocessors and one or more supplementary co-processors such as math co-processors or the like. The data storage structures discussed herein may include an appropriate combination of magnetic, optical and/or semiconductor memory, and may include, for example, RAM, ROM, flash drive, an optical disc such as a compact disc and/or a hard disk or drive.

Additionally, a software application that adapts the controller to perform the methods disclosed herein may be read into a main memory of the at least one processor from a computer-readable medium. The term "computer-readable medium," as used herein, refers to any medium that provides or participates in providing instructions to the at least one processor of the system 10 (or any other processor of a device described herein) for execution. Such a medium may take many forms, including but not limited to, non-volatile media and volatile media. Non-volatile media include, for example, optical, magnetic, or opto-magnetic disks, such as memory. Volatile media include dynamic random access memory (DRAM), which typically constitutes the main memory. Common forms of computer-readable media include, for example, a floppy disk, a flexible disk, hard disk, magnetic tape, any other magnetic medium, a CD-ROM, DVD, any other optical medium, a RAM, a PROM, an EPROM or EEPROM (electronically erasable programmable read-only memory), a FLASH-EEPROM, any other memory chip or cartridge, or any other medium from which a computer can read.

While in embodiments, the execution of sequences of instructions in the software application causes at least one processor to perform the methods/processes described herein, hard-wired circuitry may be used in place of, or in combination with, software instructions for implementation of the methods/processes of the present invention. Therefore, embodiments of the present invention are not limited to any specific combination of hardware and/or software.

It is further to be understood that the above description is intended to be illustrative, and not restrictive. For example, the above-described embodiments (and/or aspects thereof) may be used in combination with each other. Additionally, many modifications may be made to adapt a particular situation or material to the teachings of the invention without departing from its scope.

For example, in an embodiment, a system for reducing artifact bloom in a reconstructed image of an object is provided. The system includes an imaging device, and a controller. The imaging device is operative to obtain one or more slices of the object. The controller is in electronic communication with the imaging device and operative to: generate the reconstructed image based at least in part on the one or more slices; and de-bloom one or more regions within the reconstructed image based at least in part on a contrast medium enhancement across at least part of a volume of the object. In certain embodiments, the controller is further operative to de-bloom the one or more regions based at least in part on a point-spread-function. In certain embodiments, the controller is further operative to de-bloom the one or more regions based at least in part on an anti-diffusion operation. In certain embodiments, the controller is further operative to: determine an intensity threshold based at least in part on the contrast medium enhancement; and identify the one or more regions via the intensity threshold. In certain embodiments, determination of the intensity threshold is further based at least in part on a global noise value across the one or more slices. In certain embodiments, the controller is further operative to identify the one or more regions via the intensity threshold by: determining a noise value for each of the one or more slices; generating a reduced noise slice for each of the one or more slices based at least in part of the noise value of the respective slice; identifying one or more connected regions within each of the reduced noise slices; and selecting, as the identified one or more regions, one or more of the connected regions having peak intensities that exceed the intensity threshold. In certain embodiments, each of the selected one or more connected regions has a peak intensity that exceeds the intensity threshold by a predetermined amount. In certain embodiments, each of the connected regions has an area larger than a pre-defined threshold. In certain embodiments, the controller is further operative to de-bloom the one or more regions by locally de-blooming one or more sub-regions within each of the one or more regions, each of the one or more sub-regions having a peak intensity that exceeds the intensity threshold.

Other embodiments provide for a method for reducing artifact bloom in a reconstructed image of an object. The method includes determining an intensity threshold based at least in part on a contrast medium enhancement across at least part of a volume of the object. The method further includes identifying one or more regions within the reconstructed image via the intensity threshold. The method further includes de-blooming the one or more regions. In certain embodiments, de-blooming the one or more regions is based at least in part on a point-spread function. In certain embodiments, de-blooming the one or more regions is based at least in part on an anti-diffusion operation. In certain embodiments, determining the intensity threshold is further based at least in part on a global noise value across one or more slices from which the reconstructed image was generated. In certain embodiments, identifying one or more regions within the reconstructed image via the intensity threshold includes determining a noise value for each of the one or more slices; generating a reduced noise slice for each of the one or more slices based at least in part on the noise value of the respective slice; identifying one or more connected regions within each of the reduced noise slices; and selecting, as the identified one or more regions, one or more of the connected regions having peak intensities that exceed the intensity threshold. In certain embodiments, each of the selected one or more connected regions has a peak intensity that exceeds the intensity threshold by a predetermined amount. In certain embodiments, each of the connected regions has an area larger than a pre-defined threshold. In certain embodiments, de-blooming the one or more regions includes locally de-blooming one or more sub-regions within each of the one or more regions, each of the sub-regions having a peak intensity that exceeds the intensity threshold.

Yet still other embodiments provide for a non-transitory computer readable medium storing instructions. The stored instructions adapt a controller to: determine an intensity threshold based at least in part on a contrast medium enhancement across at least part of a volume of an object in a reconstructed image; identify one or more regions within the reconstructed image via the intensity threshold; and de-bloom the one or more regions. In certain embodiments, the instructions adapt the controller to de-bloom the one or more regions based at least in part on a point-spread function and an anti-diffusion operation.

Yet still other embodiments provide for a controller. The controller is operative to: generate a reconstructed image based at least in part on one or more slices of an object obtained by an imaging device; and locally de-bloom one or more calcified plaque regions within the reconstructed image.

Accordingly, as will be appreciated, by determining an intensity threshold T based on the contrast/enhancement throughout an entire volume, as opposed to a per slice-by-slice basis, some embodiments of the present invention provide for a more robust de-blooming operation for reducing blooming due to calcium and/or stents in cardiac imaging. Further, some embodiments of the present invention avoid overshooting and/or undershooting while additionally avoiding reduction in the size/width of a volume, e.g., a vessel.

Additionally, while the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, terms such as "first," "second," "third," "upper," "lower," "bottom," "top," etc. are used merely as labels, and are not intended to impose numerical or positional requirements on their objects. Further, the limitations of the following claims are not written in means-plus-function format are not intended to be interpreted as such, unless and until such claim limitations expressly use the phrase "means for" followed by a statement of function void of further structure.

This written description uses examples to disclose several embodiments of the invention, including the best mode, and also to enable one of ordinary skill in the art to practice the embodiments of invention, including making and using any devices or systems and performing any incorporated methods. The patentable scope of the invention is defined by the claims, and may include other examples that occur to one of ordinary skill in the art. Such other examples are intended to be within the scope of the claims if they have structural elements that do not differ from the literal language of the claims, or if they include equivalent structural elements with insubstantial differences from the literal languages of the claims.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

Since certain changes may be made in the above-described invention, without departing from the spirit and scope of the invention herein involved, it is intended that all of the subject matter of the above description shown in the accompanying drawings shall be interpreted merely as examples illustrating the inventive concept herein and shall not be construed as limiting the invention.

What is claimed is:

1. A system for reducing artifact bloom in a reconstructed image of an object, the system comprising:
an imaging device operative to obtain one or more slices of the object; and a controller in electronic communication with the imaging device and operative to:
  determine an intensity threshold based at least in part on the contrast medium enhancement and a global noise value across the one or more slices;
  identify one or more regions within the reconstructed image by:
    determining a noise value for each of the one or more slices;
    generating a reduced noise slice for each of the one or more slices based at least in part of the noise value of the respective slice;
    identifying one or more connected regions within each of the reduced noise slices; and
    selecting, as the identified one or more regions, one or more of the connected regions having peak intensities that exceed the intensity threshold;
  generate the reconstructed image based at least in part on the one or more slices; and
  de-bloom the identified one or more regions within the reconstructed image based at least in part on a contrast medium enhancement across at least part of a volume of the object.

2. The system of claim 1, wherein the controller is further operative to de-bloom the one or more regions based at least in part on a point-spread-function.

3. The system of claim 1, wherein the controller is further operative to de-bloom the one or more regions based at least in part on an anti-diffusion operation.

4. The system of claim 1, wherein each of the selected one or more connected regions has a peak intensity that exceeds the intensity threshold by a predetermined amount.

5. The system of claim 1, wherein each of the connected regions has an area larger than a pre-defined threshold.

6. The system of claim 1, wherein the controller is further operative to de-bloom the one or more regions by locally de-blooming one or more sub-regions within each of the one or more regions, each of the one or more sub-regions having a peak intensity that exceeds the intensity threshold.

7. A method for reducing artifact bloom in a reconstructed image of an object, the method comprising:
  determining an intensity threshold based at least in part on a contrast medium enhancement across at least part of a volume of the object and a global noise value across one or more slices, wherein the reconstructed image is based at least in part on the one or more slices;
  identifying one or more regions within the reconstructed image by:
    determining a noise value for each of the one or more slices;
    generating a reduced noise slice for each of the one or more slices based at least in part of the noise value of the respective slice;
    identifying one or more connected regions within each of the reduced noise slices; and
    selecting, as the identified one or more regions, one or more of the connected regions having peak intensities that exceed the intensity threshold; and
  de-blooming the identified one or more regions.

8. The method of claim 7, wherein de-blooming the one or more regions is based at least in part on a point-spread function.

9. The method of claim 7, wherein de-blooming the one or more regions is based at least in part on an anti-diffusion operation.

10. The method of claim 7, wherein each of the selected one or more connected regions has a peak intensity that exceeds the intensity threshold by a predetermined amount.

11. The method of claim 7, wherein each of the connected regions has an area larger than a pre-defined threshold.

12. The method of claim 7, wherein de-blooming the one or more regions comprises:
  locally de-blooming one or more sub-regions within each of the one or more regions, each of the sub-regions having a peak intensity that exceeds the intensity threshold.

13. A non-transitory computer readable medium comprising instructions that adapt a controller to:
  determine an intensity threshold based at least in part on a contrast medium enhancement across at least part of a volume of an object in a reconstructed image and a global noise value across the one or more slices, wherein the reconstructed image is based at least in part on the one or more slices;
  identify one or more regions within the reconstructed image by:
    determining a noise value for each of the one or more slices;
    generating a reduced noise slice for each of the one or more slices based at least in part of the noise value of the respective slice;
    identifying one or more connected regions within each of the reduced noise slices; and
    selecting, as the identified one or more regions, one or more of the connected regions having peak intensities that exceed the intensity threshold; and
  de-bloom the identified one or more regions.

14. The non-transitory computer readable medium of claim 13, wherein the instructions adapt the controller to de-bloom the one or more regions based at least in part on a point-spread function and an anti-diffusion operation.

15. A controller operative to:
  generate a reconstructed image based at least in part on one or more slices of an object obtained by an imaging device;
  determine an intensity threshold based at least in part on the contrast medium enhancement and a global noise value across the one or more slices of an object;
  identify one or more regions of calcified plaque by within the reconstructed image by:
    determining a noise value for each of the one or more slices;
    generating a reduced noise slice for each of the one or more slices based at least in part of the noise value of the respective slice;
    identifying one or more connected regions within each of the reduced noise slices; and
    selecting, as the identified one or more regions of calcified plaque, one or more of the connected regions having peak intensities that exceed the intensity threshold; and
  locally de-bloom the identified one or more regions of calcified plaque within the reconstructed image based at least in part on a contrast medium enhancement.

* * * * *